United States Patent
Marfurt

(10) Patent No.: US 7,323,315 B2
(45) Date of Patent: Jan. 29, 2008

(54) METHOD FOR REDUCING EFFECT OF HEMATOCRIT ON MEASUREMENT OF AN ANALYTE IN WHOLE BLOOD

(75) Inventor: Karen L. Marfurt, Mishawaka, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 439 days.

(21) Appl. No.: 10/770,235

(22) Filed: Feb. 2, 2004

(65) Prior Publication Data

US 2004/0157275 A1      Aug. 12, 2004

Related U.S. Application Data

(60) Provisional application No. 60/446,340, filed on Feb. 11, 2003.

(51) Int. Cl.
*G01N 33/00* (2006.01)

(52) U.S. Cl. .................. 435/7.25; 435/14; 435/13; 435/269

(58) Field of Classification Search .............. 436/63, 436/71, 95; 435/14, 22
See application file for complete search history.

(56) References Cited

U.S. PATENT DOCUMENTS

| | | | |
|---|---|---|---|
| 4,935,346 A | 6/1990 | Phillips | |
| 5,049,394 A | 9/1991 | Howard | |
| 5,049,487 A | 9/1991 | Phillips | |
| 5,179,005 A * | 1/1993 | Phillips et al. | 435/14 |
| 5,304,468 A | 4/1994 | Phillips | |
| 5,306,623 A * | 4/1994 | Kiser et al. | 435/14 |
| 5,789,255 A | 8/1998 | Yu | 536/95 |
| 5,948,695 A * | 9/1999 | Douglas et al. | 436/518 |
| 6,190,918 B1 * | 2/2001 | Chu et al. | 436/63 |

FOREIGN PATENT DOCUMENTS

| | | |
|---|---|---|
| EP | 1 202 059 A | 5/2002 |
| EP | 1 202 061 A | 5/2002 |
| JP | 01262470 | 10/1989 |
| JP | HEI1-262470 | 10/1989 |
| JP | 09105750 | 4/1997 |
| WO | WO 01/57239 | 8/2001 |
| WO | WO 02/14535 A2 | 2/2002 |

OTHER PUBLICATIONS

Red Cell Volume in Glycerol/Sodium Chloride/Water Mixtures, Brief Communications, Cryobiology 21, pp. 234-239 (1984).
European Search Report, Nov. 8, 2005.

* cited by examiner

*Primary Examiner*—Long V. Le
*Assistant Examiner*—N Yang
(74) *Attorney, Agent, or Firm*—Nixon Peabody LLP

(57) ABSTRACT

A method for determining the presence and/or amount of an analyte in a sample of whole blood comprises the step of treating the sample with a nonlytic hypertonic salt composition to reduce the hematocrit by reducing the size of the red blood cells. In optical detection systems, the smaller red blood cells create greater scatter, which allows a more accurate correction to be applied in a dual-wavelength detection system. In electrochemical detection systems, as well as in optical detection systems, the smaller red blood cells provide less obstruction to the diffusion of analyte and reagents in the sample, to facilitate the reactions thereof.

28 Claims, 3 Drawing Sheets

0

200

50

400

40% hematocrit

100

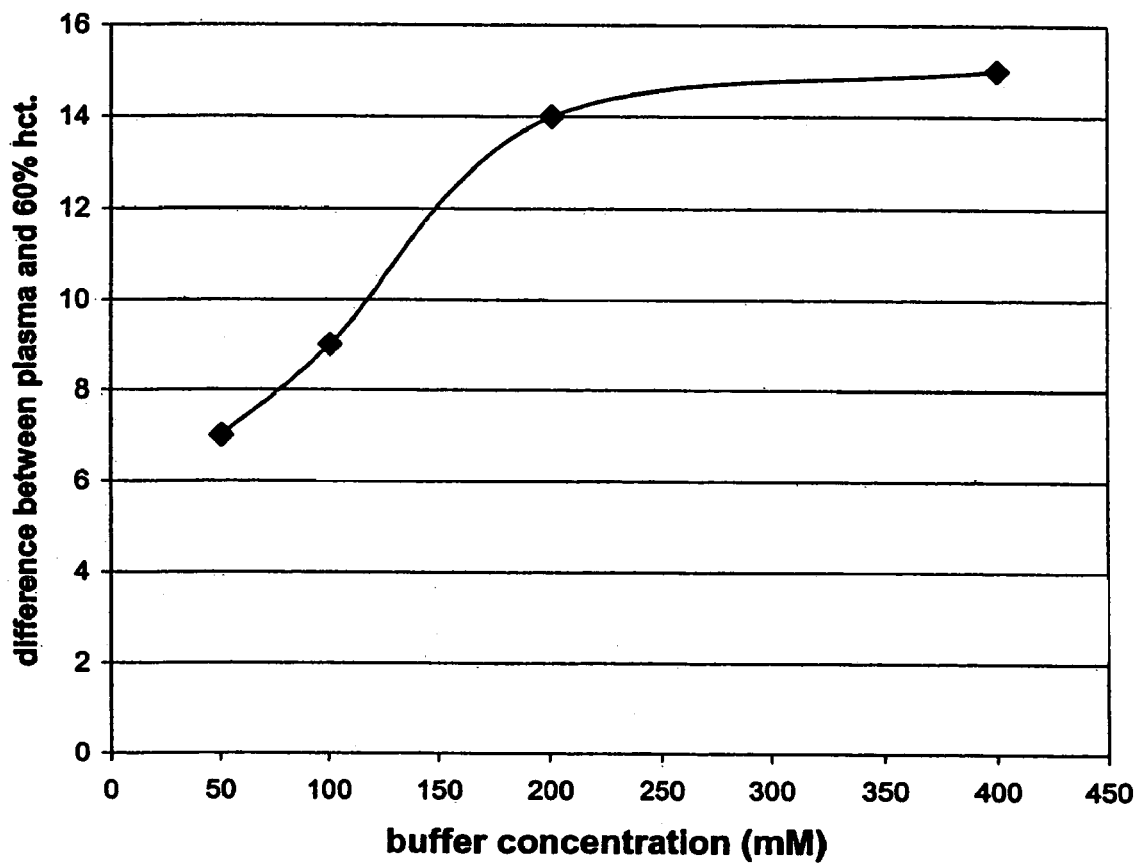

METHOD FOR REDUCING EFFECT OF HEMATOCRIT ON MEASUREMENT OF AN ANALYTE IN WHOLE BLOOD

CROSS-REFERENCE TO RELATED APPLICATION

This application claims benefit to U.S. Provisional Application No. 60/446,340, filed on Feb. 11, 2003, which is incorporated by reference in its entirety.

BACKGROUND OF THE INVENTION

This invention relates to a method for measuring the presence and/or an amount of analyte in a sample of blood with improved accuracy and precision by reducing the effect of hematocrit on the measurement. The invention further relates to a test article useful in performing the method, and test kits comprising the test article.

It has become increasingly important to medical science to be able to quantify the chemical and biochemical components in whole blood. Such ability is important in testing for exposure to hazardous materials, intoxicants, and therapeutic drugs, and in diagnostics. In some applications, it is important for a lay person to be able to perform the test outside a laboratory environment, with rapid and accurate results. For example, diabetics must test samples of their own blood for glucose several times a day to moderate their diet and medication. The test results must be both rapidly available and accurate. Assays for glucose in either plasma or whole blood can employ either oxidative or reductive chemistries that employ either colorimetric or electrochemical detection systems. Other analytes of interest in blood include cholesterol, triglycerides, ethanol, lactic acid, beta-hydroxy butyrate, ketone bodies, and fructosamine.

Test kits for the determination of glucose and other analytes in blood are well known in the art. Such test kits usually involve a test article such as a test strip or microfluidic device impregnated, coated, deposited, or printed with one or more chemicals that react in the presence of glucose to cause a dose-dependent response that may be measured by electrochemical or optical methods, or any combination thereof. Optical measurements can include transmittance, absorbance, and reflectance methods. Electrochemical measurements can include amperometric or coulometric methods.

It is well known that variations in hematocrit between whole blood samples used in diagnostic tests can interfere with accurate measurement of an analyte. Whole blood hematocrit (abbreviated hct) is a measure of the percentage of whole blood volume occupied by the red blood cells. It is also referred to as the packed cell volume, or the proportion of red blood cells to plasma. The interference caused by the hematocrit variation can arise from at least three factors: 1) interference with the detection of an optical signal used in analyte measurement by reflectance, absorbance or scatter of light; 2) interference with the rate of the chemical reaction by obstructing the diffusion of analyte within a whole blood sample; and 3) interference by reducing the amount of fluid available in a sample for adequate rehydration of a dried reagent on a test strip or other test article. Thus some test kits of the prior art require the user to dilute the sample, or require that the red blood cells be filtered out of the sample or lysed prior to applying the sample to a test device, or are designed such that these functions are carried out by the device itself without user intervention.

One series of patents relating to reducing hematocrit interference in the colorimetric determination of glucose in blood includes U.S. Pat. Nos. 4,935,346, 5,049,487, 5,049,394, 5,179,005, and 5,304,468, all assigned to Lifescan, Inc. of Mountain View, Calif., and all incorporated herein by reference in their entireties. The method disclosed therein involves taking a reflectance reading from one surface of an inert two-sided porous matrix. The matrix is impregnated with a reagent that will interact with the analyte to produce a light-absorbing reaction product when the fluid being analyzed is applied to the first surface and migrates through the matrix to the second surface. Reflectance measurements of the second surface are made at two separate wavelengths in order to eliminate interferences, and a timing circuit is triggered by an initial decrease in reflectance by the wetting of the second surface by the fluid which passes through the inert matrix. The method does not require the separation of red blood cells from serum or plasma.

U.S. Pat. No. 5,789,255, also assigned to Lifescan, Inc. and incorporated herein by reference, is entitled "Blood Glucose Strip Having Reduced Sensitivity to Hematocrit." This patent discloses a reagent strip comprising an anisotropic membrane having a sample side with relatively large pores and a testing side with relatively small pores, such that a test sample is applied to the sample side and passes through the membrane toward the testing side, while the relatively large red blood cells are filtered out of the blood sample. The membrane is impregnated with a testing agent comprising a component that reacts with glucose and oxygen to create hydrogen peroxide, a color indicator that reacts with the hydrogen peroxide, and an acrylic acid polymer that reduces the effect of the red blood cells on the glucose concentration measurement.

International Publication Number WO 01/57239 A2 entitled "Reagent test strip for analyte determination" and assigned to Lifescan, Inc. describes the use of hemolyzing agents to lyse the red blood cells so that separation of the cells from plasma is not necessary. As stated therein, "The reagent test strips of the subject invention are characterized by having at least one of the following components: a porous matrix, one or more members of an analyte oxidation signal producing system; and at least one hemolyzing agent."

Japanese Kokai Patent Application No. HEI 1[1989]-262470, entitled "Dry Type Whole-Blood Analytical Element," related to Japanese Abstract JP 01262470 entitled "Dry process total blood analytical element—used esp. for detecting a high concn. of glucose in total blood," assigned to Fuji Photo Film Co. Ltd., discloses an element for determining a given component in blood containing erythrocytes. The element comprises a reagent layer and a porous developing layer, both layers being water permeable. One of the layers contains a substance capable of forming an optically detectable substance in the presence of an analyte. The porous developing layer develops additional liquid from red blood cells to wet the other layers of the test system. The porous developing layer contains at least 5 $g/m^2$ of either NaCl or KCl.

A journal article by Pegg, D. E., "Red Cell Volume in glycerol/sodium chloride/water mixtures, *Cryobiology*, (1984), 21 (2), 234-9, discloses methods for maintaining red blood cell volume in relation to cryopreservation of cells.

It is thus one object of the invention to provide a method of analyzing a sample of whole blood for an analyte that does not require separation of the red blood cells from the whole blood sample, and a test kit and an article useful in the method.

It is yet another object of the invention to provide a method for analyzing a sample of whole blood for an analyte that reduces interferences caused by variations in hematocrit among the various blood samples analyzed, and a test kit and an article useful in the method.

It is another object of the invention to provide a method for analyzing a sample of whole blood for an analyte that does not require blood to be lysed to reduce interference by variations in hematocrit, and a test kit and an article useful in the method.

It is another object of the invention to provide a method for analyzing a sample of whole blood for an analyte that does not require blood to be diluted to reduce interference by variations in hematocrit, and a test kit and an article useful in the method.

SUMMARY OF THE INVENTION

These and other objects of the invention are met by the method of the instant invention, in which the hematocrit of a blood sample is adjusted before an analyte reading is made by treating the sample with a nonlytic hypertonic salt composition to reduce the mean cell volume of the blood cells in the sample. In particular, the method comprises the steps of (a) providing a sample of blood for qualitative or quantitative determination of an analyte, (b) treating the sample with a hypertonic salt composition to adjust the hematocrit of the sample, and (c) determining the presence and/or amount of analyte in the sample.

DESCRIPTION OF THE FIGURES

FIG. 3 is a graph showing the difference in percent reflectance for a whole blood sample at 60% hct and a corresponding plasma sample, each at various levels of NaHEPES buffer concentration.

DETAILED DESCRIPTION OF THE INVENTION

Figure 1A:
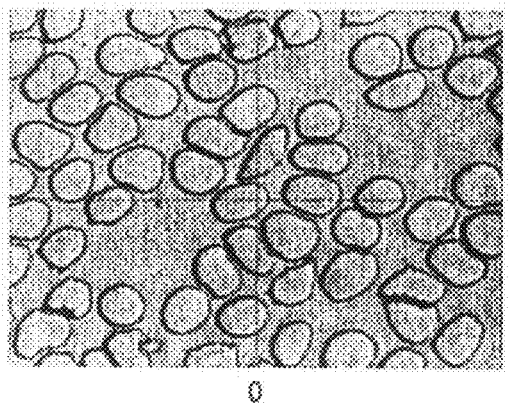
FIGS. 1A-E are photomicrographs illustrating the effects of various concentrations of hypertonic buffer salt compositions on red blood cell morphology.
Figure 1B:
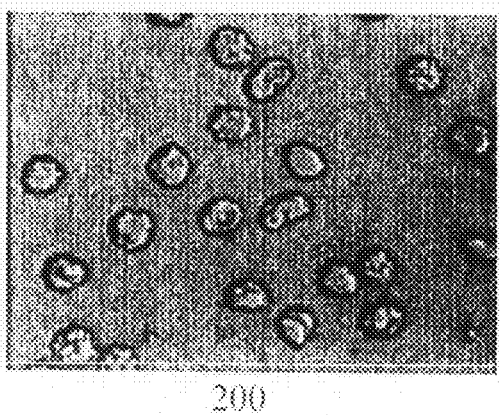
Figure 1C:
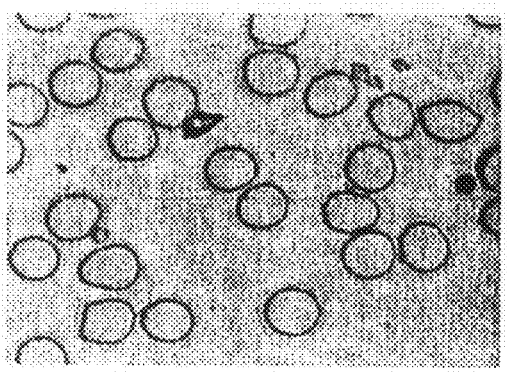
Figure 1D:
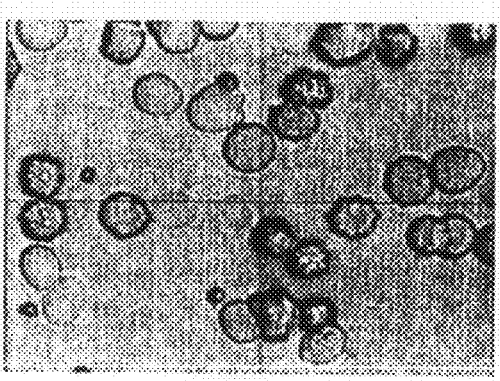
Figure 1E:
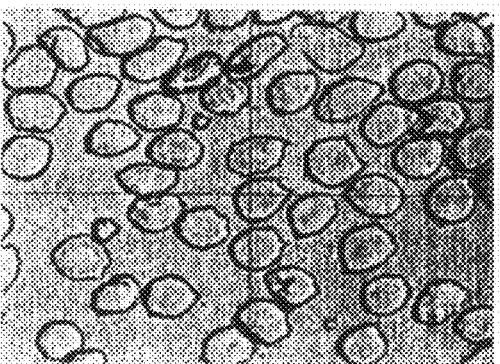

In accordance with the invention, a method is provided for determination of an analyte in a sample of blood, in which method the mean cell volume of a sample of blood is reduced to diminish the interfering effects of hematocrit on the accuracy of the determination. In accordance with the inventive method, the mean cell volume of the sample is reduced by treating the sample with a nonlytic hypertonic salt composition at some point during the diagnostic procedure. The term "hypertonic salt composition" as used in this patent means a composition of any organic or inorganic salt or salts or mixtures thereof, which composition is sufficient to create in a blood sample an osmotic pressure greater than that of an isotonic fluid. The term "nonlytic" as used in this patent means that the composition will not induce substantial lysis of the red blood cells in a sample undergoing analysis by the present method.

More particularly, the method of the invention comprises the steps of (a) providing a sample of blood for qualitative or quantitative determination of an analyte, (b) treating the sample with a nonlytic hypertonic salt composition to adjust the hematocrit of the sample, and (c) determining the presence and/or amount of analyte in the sample.

The step of treating the sample with a nonlytic hypertonic salt composition can be accomplished, for example, by adding a pre-determined amount of a nonlytic hypertonic salt composition to the sample. Preferably, however, this step is accomplished by depositing the sample (or a portion thereof) on a test article that is already provided with an appropriate amount of the nonlytic hypertonic salt composition.

The instant invention also comprises an article useful for carrying out the inventive method, which article has been treated with a hypertonic salt composition. Such an article can be in the form of a test strip that has been treated with a nonlytic hypertonic salt composition reagent, such as by impregnating, coating, depositing or printing. When a sample of blood is placed on the test strip, the salt composition will adjust the hematocrit of the sample, allowing an accurate determination of the analyte. Alternatively, such an article can be in the form of a microfluidic device having a well or chamber for receiving a sample. The nonlytic hypertonic salt composition can be either pre-deposited in the well or chamber such as during the manufacture thereof, or the nonlytic hypertonic salt composition can be carried to the well or chamber via a microchannel either from another well or chamber in the microfluidic device or from another source such as an external pump. Instruments for reading such test strips or microfluidic devices are well-known in the analytical arts and are commercially available. Such instruments are described, for example, in the previously mentioned U.S. Pat. No. 5,304,468.

The invention further relates to test kits comprising such a test strip or microfluidic device. A test kit useful for carrying out the method of the invention will comprise one or more of the articles as described, along with lances or other means to extract a blood sample from a patient, and optionally any reagents or solutions necessary for conducting the analysis of the particular analyte being determined. The invention can be used in kits intended for either home use or laboratory use, such as in a clinic or hospital.

This invention reduces the interference by red cells in the accurate determination of analytes within whole blood by reducing the size of the red blood cells. The reduction of red cell size in the method of the invention is believed to reduce interference by red cells by at least two mechanisms. First, in optical detection systems, the smaller red cells cause an increase in light scatter. While light scattered by red cells can be a source of interference, one can compensate for this interference by measuring the scattered light at a wavelength different from the wavelength at which the analyte is measured, and compensating for the measured interference. Smaller particles scatter more light than larger particles. In the method of the invention, the signal of the smaller interfering red cells is increased over native red cells. The increased scattering signal makes the measurement of the interference by the red cells more accurate, thus making the compensation for the interference by the red cells more accurate, so that the final analyte determination is more accurate.

For test kits used in optical determinations of an analyte, readings will be taken at both a first wavelength chosen for the analyte measurement and at a second wavelength that has little or no overlap with the analyte measurement wavelength. At the analyte measurement wavelength, the reading is a function of both the amount of analyte and the hematocrit by way of the induced scatter of the red blood cells present. At the second, non-analyte wavelength, the reading is a function of the hematocrit by way of the induced scatter of the red blood cells, and not substantially a function of the analyte. The reading at the second, non-analyte wavelength allows the determination of the hematocrit of the sample. The reading taken at the analyte wavelength can then be corrected to account for the hematocrit of the sample, to determine the amount of analyte in the sample. The accuracy of the analyte determination thus depends on the accuracy of the hematocrit determination. While most diagnostic tests try to decrease scatter and thus decrease the effect of hematocrit on a measurement, the applicant herein has found that, surprisingly, an increase in the amount of scatter and/or reflectance can be used in accordance with the inventive method to achieve a more accurate determination of the hematocrit in the measurement. This allows for a more accurate correction to be applied to the measurement made at the analyte wavelength, and therefore a more accurate determination of the amount of analyte in the blood sample.

Second, in both optical and electrochemical systems, smaller red cells also provide shorter diffusion paths for analyte particles to move around red cells to reach reactive areas in the analytical device; this is of particular importance in electrochemical analytical devices. Reduction in both the mean cell volume and the range of packed cell volumes among samples of differing native hematocrits reduces the interference by decreasing these diffusion paths.

The use of nonlytic hypertonic salt solution reduces the mean cell volume of the sample by reducing the particle size of the red blood cells. This can be seen in FIGS. 1a-e, which show red blood cell morphology in samples of whole blood having hematocrit levels of about 40% treated with solutions of NaHEPES at concentration levels of 0 mM, 50 mM, 100 mM, 200 mM, and 400 mM, respectively. Five hundred microliter aliquots of NaHEPES buffer prepared at 50, 100, 200, and 400 mM were added to 1.5 ml microfuge tubes and the liquid was evaporated using a SpeedVac concentrator (Savant Instruments, Inc.) at 30° C. Each aliquot of dried buffer salt was then reconstituted with whole blood samples prepared at various hematocrits. The samples of 20, 40, and 60% hematocrit whole blood were targeted and prepared by mixing packed cells and plasma. A small sample of each aliquot was used to prepare a blood smear on a glass microscope slide so that the morphology of the red blood cells could be observed under the microscope. It may be seen that at higher buffer concentrations the red blood cells take up a substantially smaller volume of the sample. These smaller red blood cells increase the scatter of light from the sample.

Figure 2:
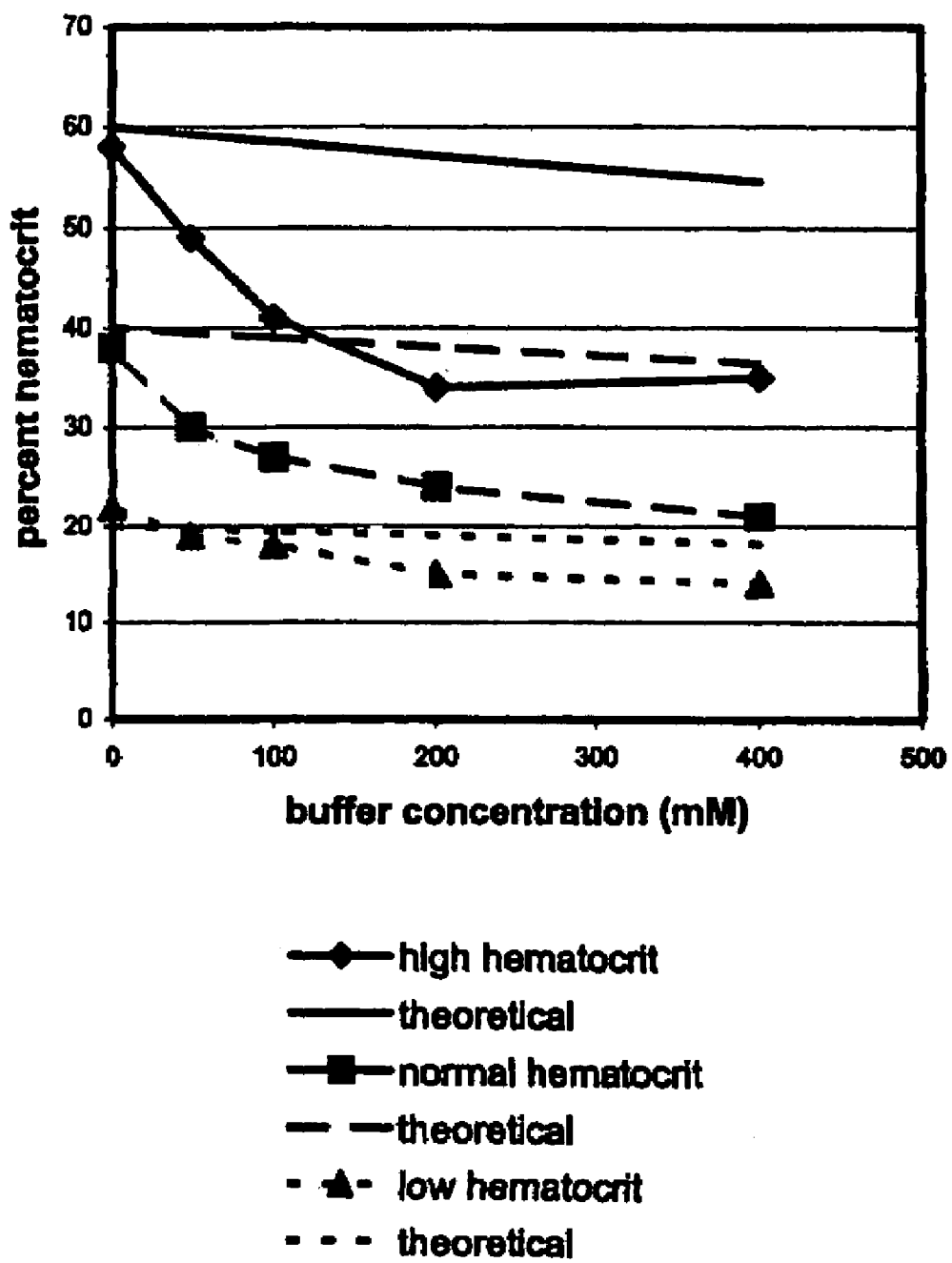
FIG. 2 is a graph showing the change in hematocrit of 20, 40, and 60 percent initial hematocrit whole blood samples at various buffer salt concentrations.

Table 1 below illustrates the effect of a hypertonic buffer salt, NaHEPES, on the hematocrit (packed cell volume). The data represent hematocrit readings taken after mixing whole blood at different hematocrit levels with different concentrations of NaHEPES buffer. The hematocrit level of each sample both before and after adding to the salt was checked using a Compur M-1100 micro-capillary reader instrument to measure the packed cells. The data in Table 1 and FIG. 2 demonstrate that, as the cell size decreases with increasing buffer salt concentration, the packed cell volume decreases, thus decreasing the hematocrit. The theoretical trend lines shown in FIG. 2 demonstrate what the expected hematocrit would be due to the volume displaced by the salt. It may be seen that the effect on the hematocrit is substantially greater than theoretically expected, and, at higher hct levels, the effect of increased buffer salt concentrations is substantially greater for higher hct levels than for lower hct levels.

FIG. 3 shows the effect of hypertonic buffer salt concentration on measured reflectance at 940 nm which was chosen as an example wavelength for the hematocrit correction using red blood cell scatter. In the graph, the vertical axis represents the difference between percent reflectance measured for plasma samples and for whole blood samples initially having 60% hct, each sample having the indicated buffer concentration. The data were collected by measuring reflectance of the mixture obtained after adding the blood samples to aliquots of glucose reagent buffered at the specified concentrations with NaHEPES, pH 7.5, using the apparatus described in co-pending patent application Ser. No. 60/373,583 filed Apr. 19, 2002. These data demonstrate the significant effect that increased buffer concentration has on the reflectance of a sample with high hct.

The method of the instant invention is also useful in non-optical determinations, such as electrochemical determinations. The smaller red blood cells pose less of an obstruction to the diffusion of analyte and reagents in a whole blood sample, such that the chemical reactions necessary for analyte determination can proceed more readily, which will yield a more accurate result.

Accordingly, the method of the instant invention comprises the steps of (a) providing a sample of blood for qualitative or quantitative determination of an analyte, (b) treating the sample with a nonlytic hypertonic salt composition to adjust the hematocrit of the sample, and (c) determining the presence and/or amount of analyte in the sample.

I claim:

1. A method for determining the presence and/or amount of an analyte in a sample of whole blood, the method comprising the steps of
    (a) providing a sample of whole blood for qualitative or quantitative determination of an analyte,
    (b) contacting the whole blood sample with a nonlytic hypertonic salt composition to adjust the hematocrit of the whole blood sample, and
    (c) detecting the presence and/or amount of analyte in the whole blood sample by measuring the analyte in the treated whole blood sample in the absence of a separation step.

2. The method of claim 1 where said analyte is selected from the group consisting of glucose, cholesterol, triglycerides, ethanol, lactic acid, beta-hydroxy butyrate, ketone bodies, and fructosamine.

3. The method of claim 1 wherein the detection of the presence and/or amount of analyte in the sample is performed by an optical detection method.

4. The method of claim 3 wherein said optical detection method is selected from the group consisting of reflectance, absorbance, and transmittance.

5. The method of claim 3 wherein a first optical measurement is made at a wavelength at which the reading is a function of the analyte and the hematocrit, a second optical measurement is made at a wavelength at which the reading is not substantially a function of the analyte, and the reading of the first measurement is corrected in accordance with the reading of the second measurement.

6. The method of claim 1 wherein the detection of the presence and/or amount of analyte in the sample is performed by an electrochemical detection method.

7. The method of claim 6 wherein said electrochemical method is a selected from the group consisting of amperometric and coulometric methods.

8. The method of claim 1 wherein said hypertonic salt composition comprises one or more organic salts, one or more inorganic salts, or any combination thereof.

9. The method of claim 1 wherein the analyte is glucose.

10. The method of claim 1 wherein treating the sample with a nonlytic hypertonic salt composition includes depositing a sufficient amount of nonlytic hypertonic salt composition on a test strip and contacting the sample with the test strip.

11. The method of claim 1 wherein treating the sample with a nonlytic hypertonic salt composition includes depositing a sufficient amount of nonlytic hypertonic salt composition on a test article and contacting the sample with the test article.

12. The method of claim 1 wherein treating the sample with a nonlytic hypertonic salt composition includes depositing a sufficient amount of nonlytic hypertonic salt composition in a microfluidic device including a well or chamber and contacting the sample in the well or chamber.

13. The method of claim 1 wherein the nonlytic hypertonic salt composition is NA-HEPES.

14. The method of claim 1 wherein the nonlytic hypertonic salt composition is prepared at at least 100 mM.

15. The method of claim 1 wherein the hypertonic salt composition comprises one or more organic salts.

16. The method of claim 1 wherein the hypertonic salt composition comprises one or more inorganic salts.

17. A method for determining the presence and/or amount of an analyte in a sample of whole blood, the method comprising the steps of
   (a) providing a sample of whole blood for qualitative or quantitative determination of an analyte,
   (b) contacting the whole blood sample with a nonlytic hypertonic salt composition prepared at at least 200 mM to adjust the hematocrit of the whole blood sample to adjust the hematocrit of the whole blood sample, and
   (c) detecting the presence and/or amount of analyte in the whole blood sample in the absence of a separation step.

18. The method of claim 17 where said analyte is selected from the group consisting of glucose, cholesterol, triglycerides, ethanol, lactic acid, beta-hydroxy butyrate, ketone bodies, and fructosamine.

19. The method of claim 18 where said analyte is glucose.

20. The method of claim 1 wherein the detection of the presence and/or amount of analyte in the sample is performed by an optical detection method.

21. The method of claim 1 wherein the detection of the presence and/or amount of analyte in the sample is performed by an electrochemical detection method.

22. The method of claim 17 wherein the nonlytic hypertonic salt composition is prepared at at least 400 mM.

23. A method for determining the presence and/or amount of an analyte in a sample of whole blood, the method comprising the steps of
   (a) providing a sample of whole blood for qualitative or quantitative determination of an analyte,
   (b) contacting the whole blood sample with a nonlytic hypertonic salt composition, and
   (c) detecting the presence and/or amount of analyte in the whole blood sample by measuring the analyte in the treated whole blood sample in the absence of a separation step.

24. The method of claim 23 wherein the nonlytic hypertonic salt composition is prepared at at least 200 mM and the analyte is glucose.

25. The method of claim 23 wherein the nonlytic hypertonic salt composition is prepared at at least 400 mM.

26. A method for determining the presence and/or amount of an analyte in a sample of whole blood, the method comprising the steps of
   (a) providing a sample of whole blood for qualitative or quantitative determination of an analyte,
   (b) contacting the whole blood sample with a nonlytic hypertonic salt composition to modify the effect of the hematocrit of the whole blood sample, and
   (c) detecting the presence and/or amount of analyte in the whole blood sample by measuring the analyte in the treated whole blood sample in the absence of a separation step.

27. The method of claim 23 wherein the nonlytic hypertonic salt composition is prepared at at least 200 mM and the analyte is glucose.

28. The method of claim 26 wherein the nonlytic hypertonic salt composition is prepared at at least 400 mM.

* * * * *